United States Patent [19]

Andrew

[11] Patent Number: 4,545,351

[45] Date of Patent: Oct. 8, 1985

[54] METHOD AND APPARATUS TO CONTROL THE LEVEL OF THE AIR-TO-FUEL WEIGHT RATIO IN AN INTERNAL COMBUSTION ENGINE

[75] Inventor: Sydney P. S. Andrew, Hartlepool, England

[73] Assignee: Imperial Chemical Industries PLC, England

[21] Appl. No.: 534,632

[22] Filed: Sep. 23, 1983

Related U.S. Application Data

[63] Continuation of Ser. No. 230,791, Feb. 2, 1981, abandoned.

[30] Foreign Application Priority Data

Feb. 7, 1980 [GB] United Kingdom ................ 8004061

[51] Int. Cl.$^4$ .............................................. F02M 7/12
[52] U.S. Cl. ...................................... 123/440; 60/276
[58] Field of Search ....................... 123/440, 489, 589; 60/276

[56] References Cited

U.S. PATENT DOCUMENTS

| | | | |
|---|---|---|---|
| 1,193,665 | 3/1935 | Holt | 123/119 E |
| 1,333,850 | 3/1920 | Kennedy | 23/232 E |
| 3,535,084 | 10/1970 | Izawa et al. | 422/93 |
| 3,667,914 | 6/1972 | Penquite | 422/93 |
| 3,669,627 | 6/1972 | Mills | 23/230 PC |
| 3,791,936 | 2/1974 | Pebler et al. | 422/94 |
| 3,825,239 | 7/1974 | Rice | 261/50 R |
| 3,841,283 | 10/1974 | Wood | 123/119 EC |
| 3,846,076 | 11/1974 | Henault | 123/32 EE |
| 3,863,615 | 2/1975 | Pagdin | 123/119 A |
| 3,885,540 | 5/1975 | Stadler | 123/119 A |
| 4,019,863 | 4/1977 | Jenkins et al. | 422/93 |
| 4,040,789 | 8/1977 | Voss et al. | 23/232 E |
| 4,113,434 | 9/1978 | Tanaka et al. | 422/93 |
| 4,130,397 | 12/1978 | Robitaille | 60/303 |
| 4,144,855 | 3/1979 | Masui et al. | 123/119 EC |
| 4,169,708 | 10/1979 | Muggli | 422/93 |
| 4,328,780 | 5/1982 | Andrew | 422/93 |

FOREIGN PATENT DOCUMENTS

| | | | |
|---|---|---|---|
| 2011064 | 9/1970 | Fed. Rep. of Germany | 23/232 E |
| 2415994 | 5/1975 | Fed. Rep. of Germany | |
| 970434 | 9/1964 | United Kingdom | 23/230 PC |
| 1285954 | 8/1972 | United Kingdom | |
| 1444362 | 7/1976 | United Kingdom | |
| 2013892 | 8/1979 | United Kingdom | 422/93 |

Primary Examiner—Andrew M. Dolinar
Attorney, Agent, or Firm—Cushman, Darby & Cushman

[57] ABSTRACT

A method and apparatus to control the level of the air-to-fuel weight ratio in an internal combustion engine includes taking from the engine a sample stream of exhaust gas which is small enough not to effect significantly the composition of the engine inlet mixture and then equilibrating the sample stream gas by reacting together the therein contained oxygen and any unburnt combustibles to produce an equilibrated gas. An untreated sample of equilibrated gas and a sample treated by addition of combustible are then provided and the untreated sample and treated sample are passed separately in time through a reaction zone maintained in conditions effective to cause mutual reactions of the added combustible and oxygen. The reaction zone contains a resistance wire acting as a catalyst wherein the reaction takes place in the immediate vicinity of a temperature sensor. The temperatures attained respectively by the untreated sample and the treated sample are then measured electrically in the reaction zone and the electrical signals are stored and compared so as to obtain a difference signal upon comparison. The difference signal is then fed to a servo mechanism actuating a gasoline feed valve in the inlet of the engine whereby the air-to-fuel weight ratio is controlled.

15 Claims, 3 Drawing Figures

METHOD AND APPARATUS TO CONTROL THE LEVEL OF THE AIR-TO-FUEL WEIGHT RATIO IN AN INTERNAL COMBUSTION ENGINE

This is a continuation of application Ser. No. 230,791, filed Feb. 2, 1981, now abandoned.

This invention relates to gas analysis and in particular to a method and apparatus to control the level of the air to fuel weight ratio in an internal combustion engine. In order to control the efficiency of combustion operations and the content of undesirable constituents, such as nitrogen oxides, in combustion effluent gas, it has become necessary to measure the oxygen content of combustion effluent gases accurately and reliably and to derive from such measurement an electrical signal. Proposals have been made to measure the oxygen content by means of an oxygen-sensitive electrode. These can be embodied in systems that are mechanically simple but they inherently suffer from the defect that the electric potential of the electrode is proportional to the logarithm of the ratio of the oxygen content of the effluent to that of air. As a result they are as sensitive to a tenfold change of oxygen partial pressure from say 0.1% to 0.01% as to a change from 10% to 1%, but are much less sensitive to a twofold change of oxygen partial pressure in the range over 0.5%, from say 1.5% to 3.0% such as would be critical in controlling operation of some types of internal combustion engine consuming a "lean" air-fuel mixture. They have the further defect that the magnitude of the electrode potential is very low unless the said ratio is very large, so that complicated electrical circuitry is required unless the desired oxygen concentration is extremely low.

In our co-pending UK application published under Ser. No. 2013892 we describe a method and apparatus for gas analysis that have a sensitivity characteristic suitable for combustion gas mixtures of moderate oxygen content, for example those liable to fluctuate in the range 0.01 to 5% by volume and also, with modification, for gases in which combustibles are present and oxygen is in deficiency if present at all. According to that application a stream of combustion effluent gas is analysed for combustible or combustion-supporting constituents by the steps of (a) forming a plurality of part streams of such gas;
(b) adding to a first part stream whichever of a combustible and a combustion-supporting constituent it is deficient in;
(c) subjecting a second, untreated, part stream and gas from step (b) to conditions effective to cause mutual reaction of combustible and combustion-supporting constituents; and
(d) measuring the temperature difference between the two part streams after subjection to those conditions.

We have now realised that that form of our method and apparatus in which the temperatures of samples of gas, respectively free from combustion and undergoing combustion, are compared using the same temperature sensor, that is, separately in time, affords greater simplicity and an improvement in performance.

According to the invention a stream of internal combustion engine effluent gas is analysed for combustible or combustion-supporting constituents by passing an untreated sample and a sample treated by addition of whichever of a combustible and a combustion-supporting constituent it is deficient in, separately in time, through a reaction zone maintained in conditions effective to cause mutual reaction of combustible and combustion-supporting constituents and containing a temperature sensor, and measuring the difference in temperature between untreated and treated samples as the result of subjection to those conditions.

The untreated and a treated sample can be provided by forming an untreated and a treated part stream and feeding these separately in time to the reaction zone. In another method a single stream is fed to the reaction zone and pulses of the combustible or combustion-supporting constituent are added to it. The change-over from one sample to another can be effected mechanically by, for example, an electromagnetically actuated valve. More conveniently it can be effected by fluidic oscillation, to avoid the use of mechanically moving parts. Conveniently in continuous operation the untreated and treated samples are fed alternatingly to the reaction zone.

In an important application of the method the effluent is the exhaust of an internal combustion engine of the reciprocating spark-ignition type. Whereas for convenience in operation such engines have for many years been designed to consume a "rich" gasoline-air mixture in which gasoline is slightly in excess, in more recently designed engines a decrease in the quantity of unburnt and partially burnt gasoline and hence a decrease in air pollution and an increase in thermal efficiency are secured by running 'lean', with a slight excess of air. Such close control of the mixture ratio in the lean range can be effected by using the analysis to correct, through a feed-back device, the setting of the carburetter or fuel injection system. A particular example of such a "lean" engine is one operating at an air to fuel weight ratio in the range 14.8 to 17.0. The linear response of the technique according to the invention makes it very suitable for detecting and correcting departures from a desired level within such a range. Engines having a compression ratio over 8.0 especially in the range 10–14 as now being developed, are very suitable for application of the method. The method can be used to detect over-lean running or over-rich running, or to control the inlet mixture within limits of richness and leanness; in the latter event the two forms of the analysis method, one with combustible addition, the other with combustion-supporting addition, can be operated side-by-side or alternatingly.

In especially useful embodiments of the invention the mutual reaction does not involve the whole of the sample but takes place mainly or exclusively in the immediate vicinity of the temperature sensor. As a result, thermal effects are minimised and the construction of the necessary apparatus can be simplified. The heat capacity of the reaction zone and sensor can be so low that the period during which each sample is passed through the reaction zone can be as short as 0.02 second or possibly even less. A typical period is in the range 0.01 to 2.0 seconds. Consequently if the temperatures are measured as electrical signals the temperature difference can be treated as an alternating current and processed to a meaningful control signal in an appropriate circuit. The circuit preferably provides phase-sensitive rectification by coupling the sample change-over frequency with the temperature alternation frequency, so as to avoid spurious temperature measurements due to other pulsations of gas flow.

The desired localised reaction can be achieved by means of a catalytic element, comprising for example Pt or Pt alloy or other platinum group metals and alloys, close to the temperature sensor. Such an element may be provided with means, such as an electrical resistance, for heating it, at least at the time of starting the analysis from cold. The temperature resulting from the mutual reaction is typically in the range 600°–1000° C.

Temperature measurement is preferably by electrical means, especially by a resistance wire or thermocouple. Using a thermocouple the catalytic element and its heater, if any, is normally separate from the sensor. A resistance wire can, however, act also as the catalyst and the heater and is therefore preferred as the temperature sensor.

Measurement of temperature difference can be carried out in a direct way but is preferably done by electrically heating the combustion-free sample to a measured extent. That is, such measurement comprises feeding an electric current to a heating element in an untreated sample, feeding no or a small current to a sample heated by combustion, and adjusting the current until the temperatures measured are equal or differ by a specified amount. This method is especially suitable using a resistance wire as temperature sensor, heater and catalyst since then the quantities of gas to be heated and the electrical load involved are minimal.

The method preferably includes subjecting the gas, before forming the untreated and treated sample, to an equilibration step in which any residual oxygen and unburnt combustibles are reacted together. The resulting higher temperature is advantageous when addition of the combustible is by evaporation of a liquid, for example gasoline or LPG. In contrast with the subsequent preferred localised reaction in presence of the temperature sensor all the gas should react in the equilibration step.

Passage of the combustion effluent gas through the equilibration zone (if present) and the addition and reaction zone is conveniently effected by suction. In an internal combustion engine the gas passes from the reaction zone preferably to the engine inlet, such as the inlet of a supercharging pump or, more commonly, to a carburetter or fuel-injection system. The stream of gas handled is normally small enough not to affect significantly the composition of the engine inlet mixture. If desired, the method can be applied to an engine operated with exhaust gas recycle, in which event the stream can be fed to the recycle pump inlet. It is also within the invention to use a suction means feeding the engine inlet but separate from means provided for normal operation of the engine.

Preferably the suction means operates at a substantially constant pressure-drop, so as to avoid significant fluctuations in the rate of flow through the zones. In an unsupercharged engine this is conveniently effected by an air intake having a variable choke the aperture area of which is automatically adjusted by a piston subjected to the pressure obtaining on the engine side of the choke. The outlet of the reaction zone is connected to the intake downstream of the variable choke. Such an air intake can be as used in the "SU" type of carburetter, in its vertical or horizontal arrangement. Other types of constant pressure-drop air intakes, including those used in carburetters, can be used.

In order to make the suction rate steadier, the gas inlet to the analysis is connected to the air intake upstream of the variable choke. This connection is downstream of any air filter or other air-treatments. By this means the pressure drop across the analysis is balanced with that across the induction air valve. Further, a more even suction can be obtained by means of a reservoir. The reservoir need, however, not be separate but can be one used for other duties such as powering brakes. Fluctuation in exhaust gas pressure at the inlet of the analysis can be smoothed out by a flow constriction.

The method is especially convenient for use with an engine having a constant pressure-drop carburetter such as of the "SU" type in which a fuel needle valve and a variable choke are automatically adjusted by a piston as mentioned. In such an engine no separate suction intake for the gas leaving the analysis is needed.

A description of the "SU" carburetter is given in "The Motor Vehicle" by Newton and Steeds, published by Iliffe, London 1953.

The invention provides, as apparatus (referred to in the description of the drawing as the "detector") for carrying out the analysis, the combination of:
(a) an inlet for combustion effluent gas;
(b) means to add to that gas a combustible constituent or a combustion-supporting constituent;
(c) a reaction zone including a temperature sensor;
(d) means to feed one-at-a-time (i) gas without addition (ii) gas containing added combustible constituents and/or (iii) gas containing added combustion-supporting constituent to that reaction zone.

The detector preferably includes at least one equilibration zone having an inlet for combustion effluent gas, ie a pre-reaction region (suitably electrically heated and/or containing an oxidation catalyst such as a platinum group metal, possibly in the form of an electrically heated wire) and an outlet for equilibrated gas.

There is preferably a flame trap between the equilibration zone (if present) and the addition means, and between the addition means and the reaction zone.

The temperature sensor preferably includes one or more electrical resistance wires. The resistance can be measured by electrically heating the wire during passage of untreated gas and measuring the power input required to raise its temperature to equality with or to a specified level of difference from the temperature of the wire during passage of treated gas. Preferably power is applied to heat both the untreated and the treated gas to some temperature above that likely to be reached by combustion alone. Such heating is preferably by the same element as is used to measure resistance, so that only the temperature of the gas in contact with the element is measured.

Alternatively the temperature sensor can be a thermocouple junction, in which event the difference in electromotive force (e.m.f.) generated is proportional to the temperature difference and thus to the oxygen or fuel content of the exhaust gas. If the electric heating method is used, the electric input power required to compensate the charge in e.m.f. is measured. Systems having a reference junction at another temperature, such as ambient air, can be used. In thermocouple systems, the electric heating element is normally distinct from the temperature sensor, but preferably the two are disposed close together.

The invention includes the combination of the detector with an electrical circuit effective to generate an electrical signal from the output of the temperature-sensor especially from the difference between its outputs in the different gases passed over it. Such a circuit typically includes a memory to store the value measured in one sample for comparison with the value measured in a later sample. If the alternation of samples is rapid enough the succession of electrical signals can be handled as an alternating current, as mentioned above.

The detector and electrical circuits can be combined further with means to give a warning to a human operator or, more usefully, to adjust the inlet air-to-fuel ratio of the combustion operation. The adjustment involves a simple electromechanical actuator and need not be detailed. When the air/fuel mixture is produced in an "SU" type carburetter, adjustment can be applied to the screw mounting of the nozzle of the needle valve or to the partial vacuum chamber controlling the position of the piston and thus the setting of the choke and the needle of the valve. The electrical circuits can be programmed to take account of the differing air-to-fuel ratios according to driving conditions; a computer controlling both the engine air-to-fuel ratio and transmission gear ratio is envisaged.

Thus the invention comprises an internal combustion engine with means for inlet air-to-fuel ratio control by the method or apparatus described herein. Particularly it includes the flow connections from the exhaust to the inlet of the detector, and from the detector to the engine inlet, in preference to an ejector or suction pump. The engine is especially one designed to operate at the air-to-fuel ratio and compression ratio specified above. The feed of fuel to the exhaust gas (if such a feed is used) can be effected by a connection to the engine fuel system, for example, by means of a wick leading to the carburetter float chamber, which can provide sufficient fuel to saturate the gas at the operating temperature and pressure. If an air feed is required, this can be effected by carburetter suction. The zones and their intervening flame traps can be provided in a single vessel, which thus can be compactly disposed in the engine compartment of an automobile.

Preferred embodiments of the detector according to the present invention are shown in accompanying drawings wherein.

Figure 1:
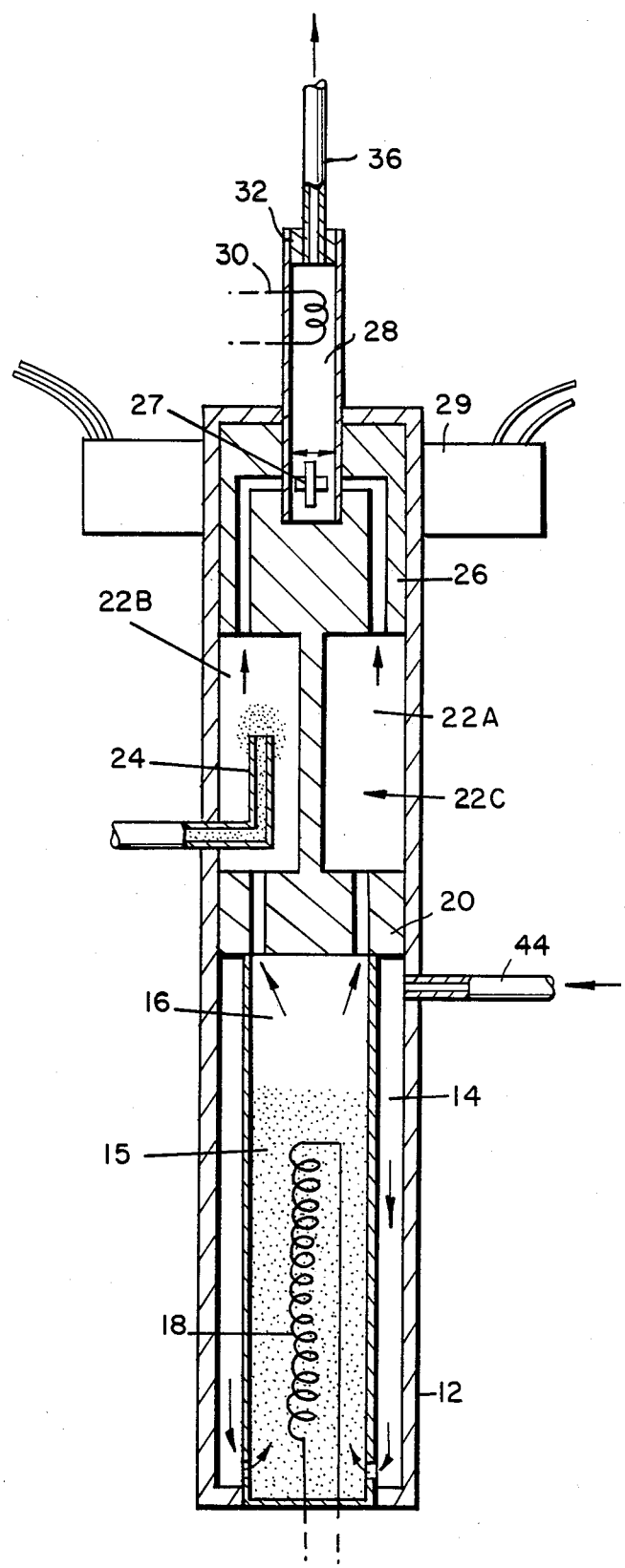
FIG. 1 is a vertical diagrammatic cross sectional view of one embodiment of the detector according to the present invention.
Figure 2:
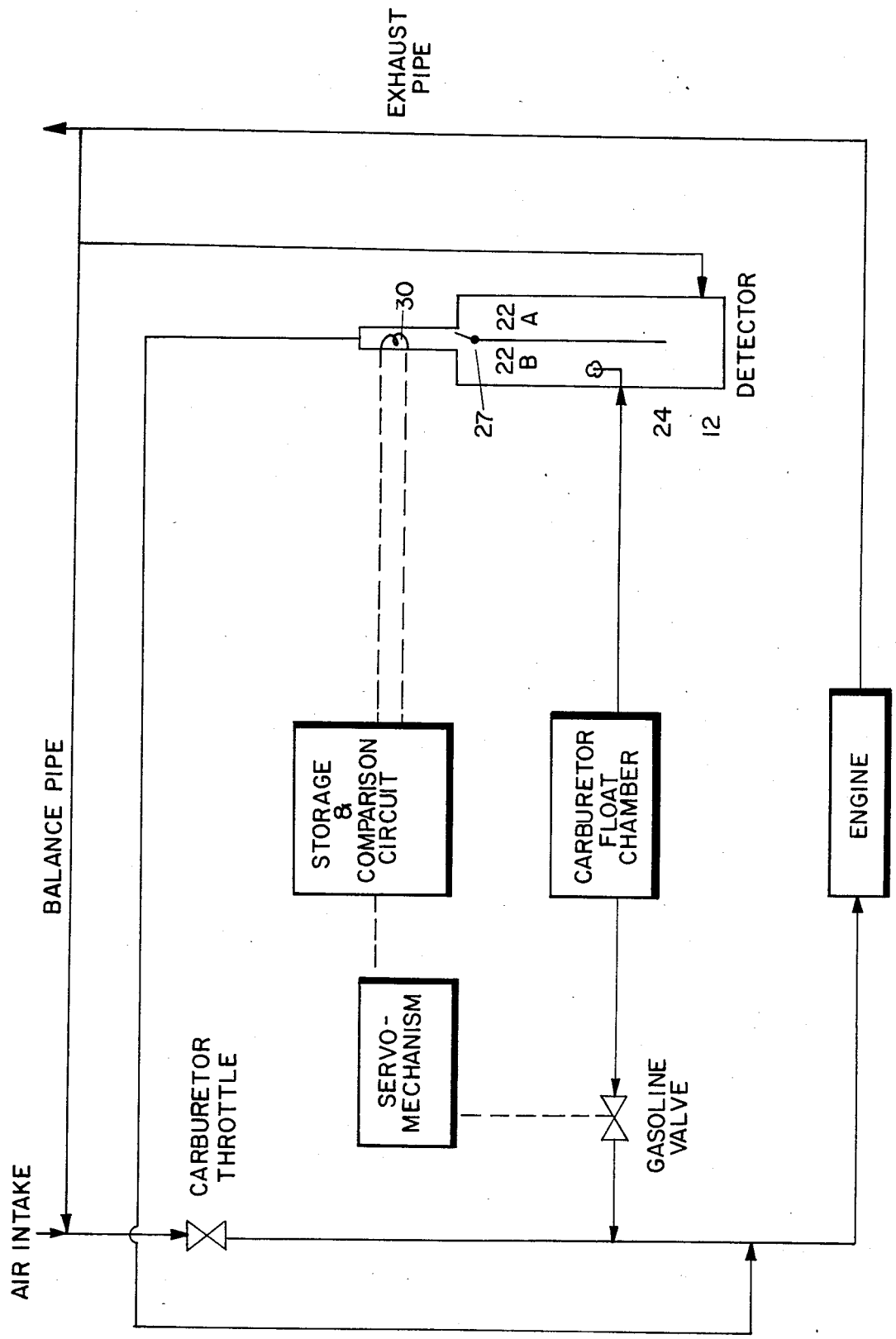
FIG. 2 is a schematic diagram showing the relationship of the detector of FIG. 1 relative to an internal combustion engine.

The detector comprises a cylindrical vessel 12 formed essentially with the following chambers:

14, which is a preheat chamber;

16, which is a reaction chamber containing catalyst 15 forming the equilibration zone and heated by electric heater 18. Flame trap 20, a metal block having two (or possibly three) narrow passages in it, closes the end of chamber 16 and constitutes a flow-dividing means;

22A and 22B, which form the addition zones, each fed by one of the passages in flame trap 20. As shown, chamber 22A has no means for adding anything and thus carries the untreated gas stream. Chambers 22B is equipped with wick saturator 24 feeding gasoline into the gas stream. If desired, a third chamber 22C with air addition means could be used, or such a chamber could be used in place of 22B if departure from lean to rich engine feed is to be detected. Flame trap 26, a metal block having two (or possibly three) narrow passages in it, closes the downstream end of chambers 22;

28, which forms the reaction zone. This may be formed in the same metal block providing flame trap 26. If desired, one of chambers 28 can communicate with chamber 22C, whether used as a third chamber or as an air-addition chamber instead of a fuel-addition chamber. Chamber 28 is heated by a hot platinum wire 30, which both provides the heat necessary to cause reaction to take place and acts as a catalyst and as a sensor of the temperature of the gas in immediate contact with it. Chamber 28 is closed at its downstream end by flame trap 32.

Gases from an engine exhaust pipe enter the detector via line 44. The gases are preheated in chamber 14 and then pass into equilibration chamber 16 where any $H_2$, CO and residual hydrocarbons react with any residual oxygen over catalyst 15. Fuel from the engine carburetter float chamber is added at 24 to the part stream entering chamber 22B but not 22A. The two part streams then pass alternatingly into chamber 28 under the control of two-way valve 27 actuated by electromagnet 29. If the exhaust gas contains excess oxygen, combustion takes place in chamber 28 in the slug of gas that has entered from chamber 22B and raises the temperature to a higher level than that of the preceding slug of gas from chamber 22A, thus increasing the resistance of wire 30B to a higher level than just previously. (An analogous temperature increase would occur if the exhaust gas contained excess combustible material and air were added in chamber 22C). An electrical signal representing such temperature is stored and successive values are compared in a suitable circuit. The reacted gases leave the detector under the suction of the partial vacuum in inlet pipe of an SU-type carburetter. As in our co-pending application there is a pipe balancing the pressure-drop through the detector with that across the induction air valve of the carburetter.

The resistance-measuring circuit may feed a servomechanism (not shown) actuating a throttle valve and/or a gasoline inlet valve in the carburetter.

Since there is only one chamber 28, the apparatus is simpler than the twin chamber detector specifically described in our published co-pending U.K. application Ser. No. 2013892. Since there is only one wire 30, the measured temperature is not subject to differences of response by different wires. When the streams are changed at the specified rate, the amplitude of the resulting intermittent electric current is proportioned to the temperature difference. The electrical circuit includes phase-sensitive rectification by coupling the sample change-over frequency with the temperature alternation frequency, and thus avoids producing a control signal as a result of temperature changes due for example to changes in gas flow rate.

Figure 3:
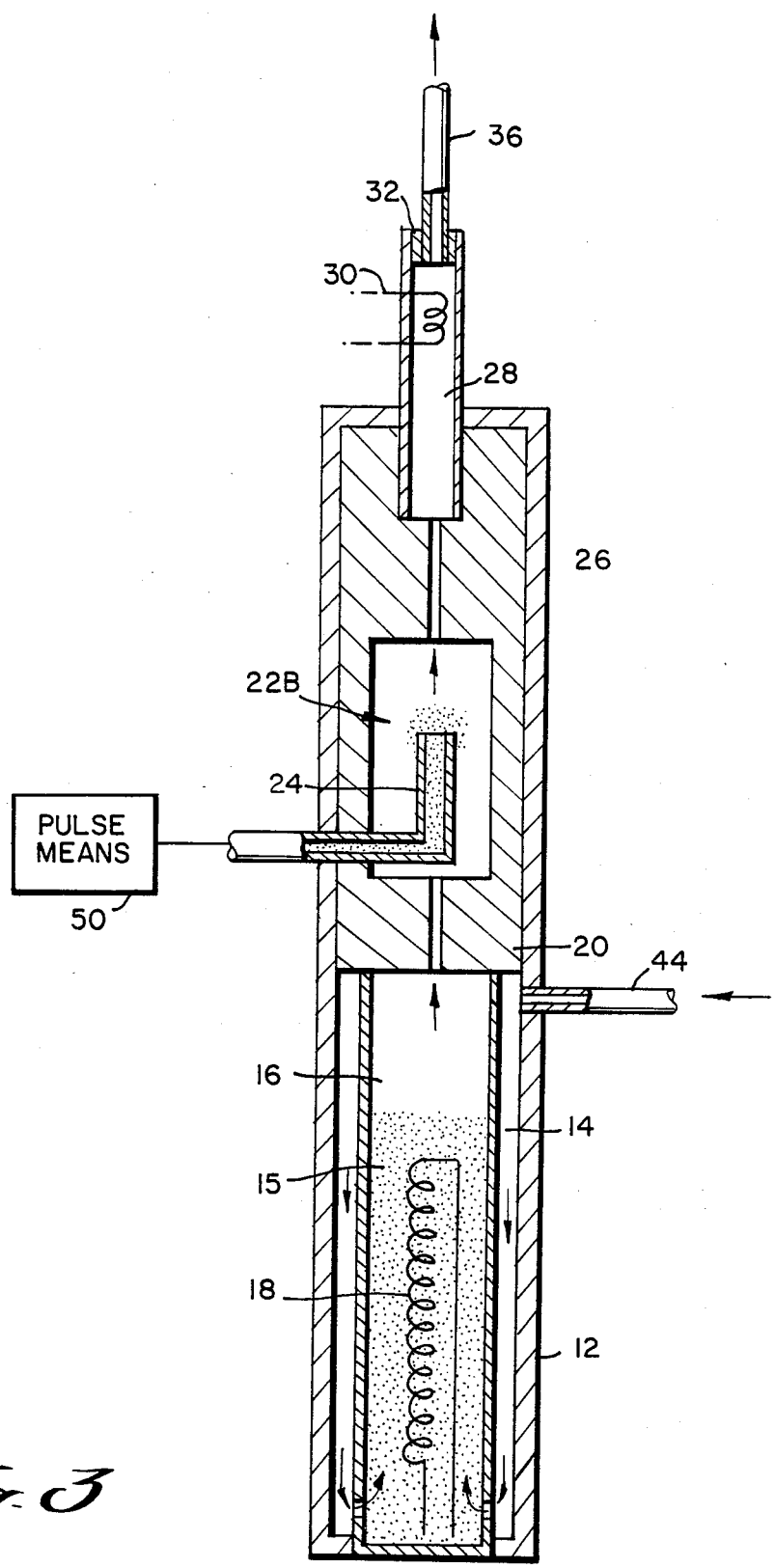
FIG. 3 is a vertical diagrammatic cross sectional view of another embodiment of the detector according to the present invention.

The detector of the present invention described above with reference to FIG. 1 can also be utilized in such a manner that a single stream of equilibrated gas is formed and then passed to reaction zone 28, as can be seen by reference to the embodiment of the invention shown in FIG. 3. As can be seen, the detector of FIG. 3 is similar to that shown in accompanying FIG. 1 with the exceptions that addition zone 22A, chamber 22C, valve 27 and electromagnet 29 are omitted. It is also advantageous in the embodiment of FIG. 3 to pulse the gasoline entering chamber 22B by suitable pulse means 50.

I claim:

1. A method of controlling at a level in the lean range 14.8 to 17.0 the air-to-fuel weight ratio of the mixture fed to the inlet of a gasoline fueled internal combustion engine, said method comprising the steps of:
(a) taking, by means of the suction at said inlet, a sample stream of exhaust gas from said engine, said stream being small enough not to affect significantly the composition of the engine inlet mixture;
(b) equilibrating said sample stream gas by reacting together the therein contained oxygen and any unburnt combustibles, whereby to produce an equilibrated gas containing only the oxygen in excess of the fuel in the inlet mixture fed to the engine;
(c) providing an untreated sample of said equilibrated gas and a sample treated by addition of combustible thereto;
(d) passing said untreated sample and said treated sample separately in time through a reaction zone maintained in conditions effective to cause mutual reaction of said added combustible and said oxygen, said reaction zone containing a resistance wire acting as a catalyst and temperature sensor and said reaction taking place in the immediate vicinity of the temperature sensor;
(e) measuring electrically the temperatures attained by respectively said untreated sample and said treated sample in said reaction zone;
(f) storing and comparing the electrical signals representing said respective temperatures to obtain a difference signal; and
(g) feeding the difference signal from said comparison to a servo mechanism actuating a gasoline feed valve in said inlet of said engine.

2. A method according to claim 1 which comprises feeding an untreated part stream and a treated part stream of said equilibrated gas alternatively to said reaction zone.

3. A method according to claim 1 which comprises forming a single stream of said equilibrated gas and adding pulses of combustible thereto, whereby to obtain a stream alternating in composition, and feeding said stream to the reaction zone.

4. A method according to claim 1 in which the combustible added to the equilibrated gas is gasoline, the engine inlet includes a carburetor and the gasoline is added to the equilibrated gas by means of a wick leading to the float chamber of said carburetor.

5. A method according to claim 1 in which each sample is passed through the reaction zone for a period in the range 0.1 to 2.0 second.

6. A method according to claim 1 in which in step (e) the temperature is measured by electrically heating the wire during passage of untreated gas and measuring the power input required to raise its temperature to equality with or to a specified level of difference from the temperature of the wire during passage of treated gas.

7. A method according to claim 6 which comprises applying power to the resistance wire to heat both the untreated and the treated gas to a temperature above that likely to be reached by combustion alone.

8. A method according to claim 1 in which in step (d) the frequency of sample change-over is coupled by phase sensitive rectification with the temperature alternation frequency recorded in step (f) whereby to avoid spurious temperature measurements.

9. An internal combustion engine to be fueled with gasoline at an inlet air-to-fuel weight ratio in the range 14.8 to 17.0 and including means for maintaining said ratio in said range, said ratio maintaining means comprising:
(a) air fuel inlet means including a first branch pipe providing suction;
(b) an exhaust pipe including a second branch pipe providing an exhaust gas sample stream;
(c) a detector unit having an inlet connected to said second branch pipe and an outlet connected to said first branch pipe, the flow capacity of said detector unit and connections being such that the gas flow will not affect significantly the composition of the engine inlet mixture, said detector unit defining serially the following zones:
  (i) an equilibration zone containing at least one of an electric heating means and an oxidation catalyst and effective to cause reaction of oxygen and any unburnt combustibles in the exhaust and gas;
  (ii) an addition zone including means to add a combustible to the effluent of the equilibration zone;
  (iii) means to feed one-at-a-time untreated equilibration zone effluent and such effluent containing added combustible to a reaction zone;
  (iv) said reaction zone, which includes a resistance wire effective to act as a heater, catalyst for the reaction and a temperature sensor, whereby reaction takes place in the immediate vicinity of the temperature sensor, and said sensor provides electrical signals representing the temperature;
(d) means for storing said electrical signals and for comparing said electrical signals to obtain a difference signal;
(e) servo means responsive to the difference signal representing the temperature increase due to oxidation of the added combustible and actuating a gasoline feed valve at the engine inlet.

10. An engine according to claim 9 further comprising an electrical circuit including phase-sensitive rectification means for coupling the sample change over frequency with the temperature alteration frequency.

11. An engine according to claim 9 in which feeding means (iii) is effective to pass each sample through the reaction zone for a period in the range 0.1 to 2.0 second.

12. An engine according to claim 9 in which means (iii) divides the gas leaving the equilibration zone into two part streams, adds to one part stream said combustible and leaves the other part stream untreated.

13. An engine according to claim 9 in which said added combustible is gasoline and is added to the equilibrated gas by a wick saturated leading to the float chamber of the engine carburetor.

14. An engine according to claim 9 in which the equilibration zone, addition zone, feeding means and reaction zone are arranged within a single detector body, a first flame trap is disposed between the equilibration zone and the addition means and a second flame trap between the addition means and the reaction zone.

15. An engine according to claim 9 wherein said temperature sensor includes means for measuring the temperature by electrically heating the wire during passage of untreated gas and measuring the power input required to raise its temperature to equality with or to a specified level of difference from the temperature of the wire during passage of treated gas.

* * * * *